US012465123B2

(12) United States Patent
Park et al.

(10) Patent No.: US 12,465,123 B2
(45) Date of Patent: Nov. 11, 2025

(54) CARRYING CASE

(71) Applicant: Jong Min Park, Suwon-si (KR)

(72) Inventors: Jong Min Park, Suwon-si (KR); Sang Gyou Park, Suwon-si (KR)

(73) Assignee: Jong Min Park, Suwon-si (KR)

( * ) Notice: Subject to any disclaimer, the term of this patent is extended or adjusted under 35 U.S.C. 154(b) by 305 days.

(21) Appl. No.: 18/031,615

(22) PCT Filed: Sep. 1, 2021

(86) PCT No.: PCT/KR2021/011727
§ 371 (c)(1),
(2) Date: Apr. 13, 2023

(87) PCT Pub. No.: WO2022/080664
PCT Pub. Date: Apr. 21, 2022

(65) Prior Publication Data
US 2023/0380558 A1 Nov. 30, 2023

(30) Foreign Application Priority Data
Oct. 13, 2020 (KR) ........................ 10-2020-0131946

(51) Int. Cl.
*A45C 11/00* (2006.01)
*A41D 13/11* (2006.01)
(Continued)

(52) U.S. Cl.
CPC .......... *A45C 11/00* (2013.01); *A41D 13/1161* (2013.01); *A45C 13/1069* (2013.01);
(Continued)

(58) Field of Classification Search
CPC . A41D 13/1161; A45C 11/00; A45C 13/1069; A45C 2011/007; A45C 7/00;
(Continued)

(56) References Cited

U.S. PATENT DOCUMENTS 10,888,798 B1 * 1/2021 Vaca ...................... A63H 33/00
11,583,043 B2 * 2/2023 Tovias ................. A44C 15/003
(Continued)

FOREIGN PATENT DOCUMENTS

CN 207898066 U 9/2018
JP 6757999 B1 9/2020
(Continued)

OTHER PUBLICATIONS

International Search Report for PCT/KR2021/011727 mailed Dec. 23, 2021 from Korean Intellectual Property Office.

*Primary Examiner* — Nathan J Newhouse
*Assistant Examiner* — Matthew T Theis
(74) *Attorney, Agent, or Firm* — Revolution IP, PLLC

(57) ABSTRACT

The present invention provides a carrying case including: a first main body having a semi-ellipsoidal shell shape; and a second main body having a semi-ellipsoidal shell shape corresponding to the first main body so that the second main body is coupled to the first main body to define an ellipsoid, in which a coupling end of the first main body, which is coupled to the second main body, has two or more pairs of connected convex portions and two or more pairs of connected concave portions, such that a lateral side at a major axis side has a taegeuk shape, in which a coupling end of the second main body has concave portions formed at positions corresponding to the convex portions of the first main body, and convex portions formed at positions corresponding to the concave portions of the first main body.

5 Claims, 9 Drawing Sheets

(51) Int. Cl.

| | |
|---|---|
| ***A45C 13/10*** | (2006.01) |
| ***A45F 5/00*** | (2006.01) |
| ***A45F 5/02*** | (2006.01) |
| ***A61L 2/10*** | (2006.01) |
| ***A61L 2/26*** | (2006.01) |

(52) U.S. Cl.
CPC .............. *A45F 5/004* (2013.01); *A45F 5/021* (2013.01); *A61L 2/10* (2013.01); *A61L 2/26* (2013.01); *A45C 2011/007* (2013.01); *A45F 2005/006* (2013.01); *A45F 2005/008* (2013.01); *A61L 2202/11* (2013.01); *A61L 2202/23* (2013.01)

(58) Field of Classification Search
CPC .......... A45F 2005/006; A45F 2005/008; A45F 5/004; A45F 5/021; A61L 2/10; A61L 2/20; A61L 2/26; A61L 2202/11; A61L 2202/23
USPC ........................................... 224/162; 383/907
See application file for complete search history.

(56) References Cited

U.S. PATENT DOCUMENTS

| | | | |
|---|---|---|---|
| 2016/0022045 | A1 | 1/2016 | Lee |
| 2019/0069066 | A1 | 2/2019 | Song et al. |
| 2020/0335371 | A1 | 10/2020 | Chuang et al. |

FOREIGN PATENT DOCUMENTS

| | | | |
|---|---|---|---|
| KR | 10-2019-0021033 | A | 3/2019 |
| KR | 10-2020-0061325 | A | 6/2020 |

* cited by examiner

CARRYING CASE

CROSS REFERENCE TO PRIOR APPLICATIONS

This application is the 35 U.S.C. 371 national stage of international application PCT/KR2021/011727 filed on Sep. 1, 2021 which claims priority to Korean Patent Application No. 10-2020-0131946 filed on Oct. 13, 2020. The entire contents of each of the above-identified applications are hereby incorporated by reference.

TECHNICAL FIELD

The present invention relates to a carrying case for storing an item such as a mask.

BACKGROUND ART

It is essential to wear a mask to prevent the spread of infectious diseases caused by bacteria or viruses such as the coronavirus. It is necessary to store the mask safely while using the mask and prevent contamination caused by hands.

To address these issues, there has been a need to develop a case for hygienically storing and conveniently carrying an item, which is vulnerable to contamination and needs to be worn on a sensitive area, or an item that is small but essential.

DISCLOSURE

Technical Problem

An object of the present invention provided to meet the above-mentioned need is to provide a carrying case capable of being assembled or disassembled so that a target item may be stored or taken out to prevent contamination caused by bacteria or viruses.

Another object of the present invention is to provide a mask-integrated carrying case capable of allowing a mask to be easily stored or taken out.

Still another object of the present invention is to provide a carrying case capable of allowing a user to wear the case when wearing the mask.

Yet another object of the present invention is to provide a carrying case capable of sterilizing an item stored in the carrying case at the time of storing the item.

Technical Solution

The present invention provides a carrying case including:

a first main body having a semi-ellipsoidal shell shape; and a second main body having a semi-ellipsoidal shell shape corresponding to the first main body so that the second main body is coupled to the first main body to define an ellipsoid, in which a coupling end of the first main body, which is coupled to the second main body, has two or more pairs of connected convex portions and two or more pairs of connected concave portions, such that a lateral side at a major axis side has a taegeuk shape, in which a coupling end of the second main body has concave portions formed at positions corresponding to the convex portions of the first main body, and convex portions formed at positions corresponding to the concave portions of the first main body.

In addition, the present invention provides a carrying case including:

a first main body having a semi-polyhedral shell shape; and a second main body having a semi-polyhedral shell shape corresponding to the first main body so that the second main body is coupled to the first main body to define a polyhedron, in which a coupling end of the first main body, which is coupled to the second main body, has two or more pairs of connected convex portions and two or more pairs of connected concave portions, such that a lateral side at a major axis side has a taegeuk shape, in which a coupling end of the second main body has concave portions formed at positions corresponding to the convex portions of the first main body, and convex portions formed at positions corresponding to the concave portions of the first main body.

One or two cut-out grooves having a preset length perpendicular to the coupling end may be formed at one coupling end or two opposite coupling ends of the first main body and the second main body.

Coupling members may be respectively provided on the first main body and the second main body, and a connection part connected to a mask strap may be coupled to the coupling members.

The connection part may include: couplers coupled to central regions of the first main body and the second main body; connection strings respectively coupled to the couplers; and connection rings coupled to ends of the connection strings so as to be connected to the mask strap.

A connection ring protection cover having a folded pipe shape may be penetratively coupled to the connection string and covers the connection ring.

Reel-shaped storage boxes may be respectively disposed inside the first main body and the second main body, and the connection strings may be semi-automatically wound in the reel-shaped storage boxes.

Magnets having corresponding polarities may be embedded in peripheries of the coupling ends of the first and second main bodies.

One or more guide rods may be respectively coupled to inner surfaces of the first and second main bodies so as to be parallel to a major axis of the ellipsoid, and rollers may be penetratively coupled to the guide rods, respectively.

Advantageous Effects

According to the embodiment of the present invention configured as described above, it is possible to provide the carrying case capable of being assembled or disassembled so that the target item may be stored or taken out to prevent contamination caused by bacteria or viruses.

In addition, according to the embodiment of the present invention, it is possible to provide the mask-integrated carrying case capable of allowing the mask to be easily stored or taken out.

In addition, according to the embodiment of the present invention, it is possible to provide the carrying case capable of allowing the user to wear the case when wearing the mask.

In addition, according to the embodiment of the present invention, it is possible to provide the carrying case capable of sterilizing the item stored in the carrying case at the time of storing the item.

MODES OF THE INVENTION

Figure 1:
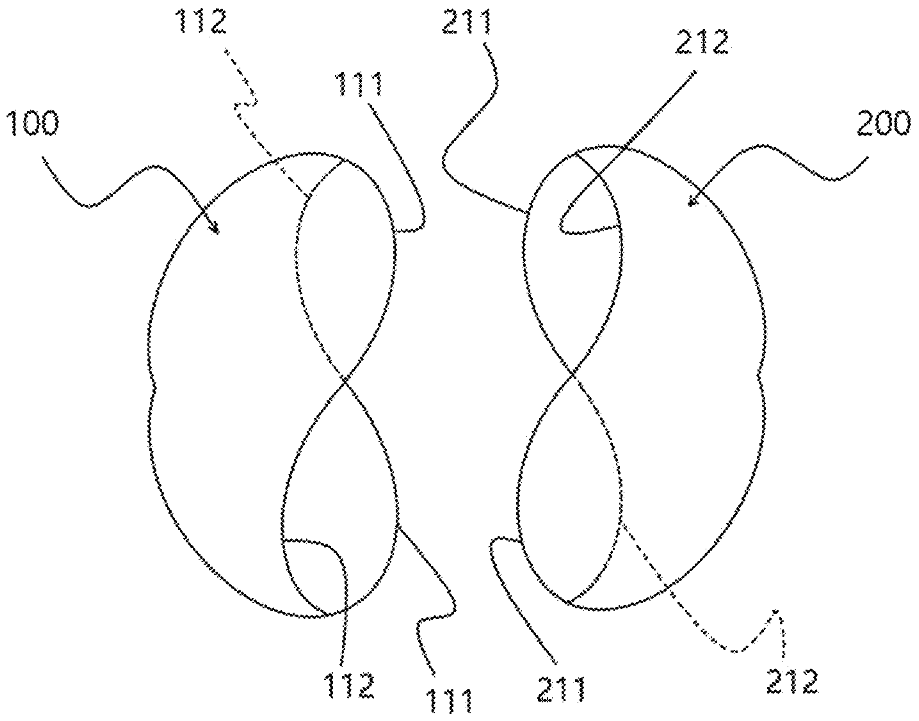
FIG. 1 is a schematically illustrating a main body of a carrying case according to an embodiment of the present invention.

Hereinafter, exemplary embodiments of the present invention will be described in detail with reference to the accompanying drawings. First, in giving reference numerals to constituent elements of the respective drawings, it should be noted that the same constituent elements will be designated by the same reference numerals, if possible, even though the constituent elements are illustrated in different drawings. In addition, in the description of the present invention, the specific descriptions of publicly known related configurations or functions will be omitted when it is determined that the specific descriptions may obscure the subject matter of the present invention.

Figure 2:
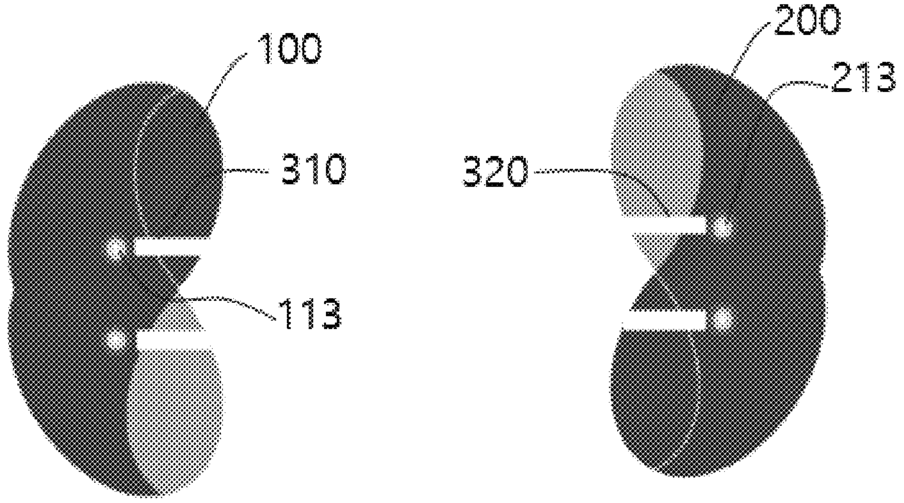
FIG. 2 is a view schematically illustrating a carrying case according to a first embodiment of the present invention.

FIG. 1 is a schematically illustrating a main body of a carrying case according to an embodiment of the present invention, and FIG. 2 is a view schematically illustrating a carrying case according to a first embodiment of the present invention. As illustrated, a carrying case 1000 according to an embodiment of the present invention has an ellipsoidal shell shape. The carrying case 1000 defines an ellipsoidal shell by coupling a first main body 100 having a semi-ellipsoidal shell shape and a second main body 200 having a shape corresponding to the first main body 100. A coupling end of the first main body 100, which is coupled to the second main body 200, has two or more pairs of connected convex portions 111 and two or more pairs of connected concave portions 112, such that a lateral side at a major axis side has a taegeuk shape. The second main body 200 is formed in a semi-ellipsoidal shell shape corresponding to the first main body 100. A coupling end of the second main body 200 has concave portions 212 disposed at positions corresponding to the convex portions 111 of the first main body 100, and convex portions 211 disposed at positions corresponding to the concave portions 112 of the first main body 100. The concave portions 212 and the convex portions 211 are connected to one another, such that a lateral side of the second main body 200 defines a taegeuk shape corresponding to the first main body 100. The coupling ends have the taegeuk shapes by means of the continuous concave portions 112 and 212 and the continuous convex portions 111 and 211 of the first main body 100 and the second main body 200. It is possible to adjust the ease of engagement and disengagement of the first main body 100 and the second main body 200 by adjusting curvatures of the concave portions 112 and 212 and the convex portions 111 and 211. That is, the curvature of each of the concave portions 112 and 212 and the convex portions 111 and 211 may be larger than a curvature of an ellipsoid defined by the carrying case 100. In particular, a radius of curvature of each of the convex portions 111 and 211 may be smaller than ½±10% of a minor axis of the ellipsoid. In case that the first main body 100 and the second main body 200 are made of a material such as silicone excellent in elasticity or flexibility, the radius of curvature may be set to be 60% of the minor axis. In case that the curvature of each of the convex portions 111 and 211 has a predetermined value or more, the first main body 100 and the second main body 200 are not easily separated only by pulling the coupling ends in a vertical direction to open the first main body 100 and the second main body 200 in the state in which the first main body 100 and the second main body 200 are coupled by inserting the convex portions 111 and 211 into the concave portions 111 and 211. When the first main body 100 and the second main body 200 are rotated in opposite directions, the first main body 100 and the second main body 200 may be easily separated along slopes of the concave and convex portions. The first main body 100 and the second main body 200 may be coupled by adjusting the curvatures without a separate fastening means.

As illustrated in FIG. 2, connection parts to be described below are provided at one side of the first main body 100 and one side of the second main body 200 by coupling members 113 and 213, such as rivets, that respectively penetrate the first main body 100 and the second main body 200. The connection parts, which may be connected to straps of a mask, are coupled to the coupling members 113 and 213. One or two cut-out grooves 310 and 320 are formed at one coupling end or two opposite coupling ends of the first main body 100 and the second main body 200, and the cut-out grooves 310 and 320 each have a preset height perpendicular to the coupling end. A string of the connection part or the strap s of the mask may pass through the cut-out grooves 310 and 320 when the mask is taken out of the case 100 and used.

Although not illustrated, outer surfaces of the first main body 100 and the second main body 200 extend from one side of the peripheries of the coupling ends, and inner surfaces of the first main body 100 and the second main body 200 extend from the other side of the peripheries of the coupling ends, such that stepped portions, which may engage with each other, are formed, and the first main body 100 and the second main body 200 may be coupled to each other. The stepped portion may be formed over the entire periphery of the coupling end or partially formed at the periphery of the coupling end. Magnets, which correspond to each other, may be embedded in the coupling ends, such that the end of the first main body 100 and the end of the second main body 200 may be coupled to each other by a magnetic force. Other fastening means, which are not mentioned above, may be used to couple the first main body 100 and the second main body 200. The coupling end of the first main body 100 and the coupling end of the second main body 200 are formed in taegeuk shapes corresponding to each other, such that the first main body 100 and the second main body 200 may be easily coupled to each other without being coupled along the slopes when the first main body 100 and the second main body 200 are coupled. The first main body 100 and the second main body 200 may be made of silicone or polymer.

Figure 3:
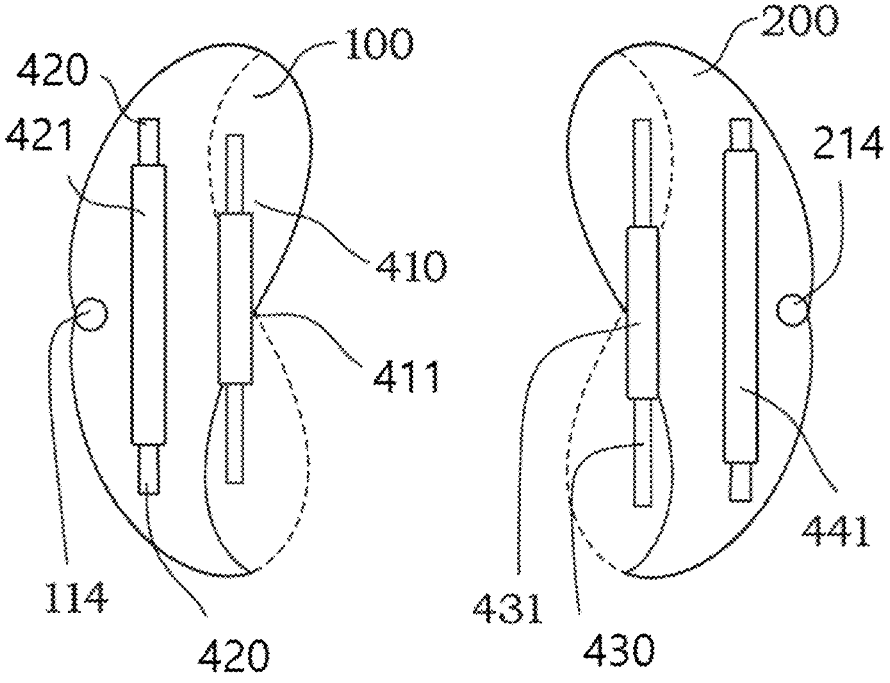
FIG. 3 is a view schematically illustrating a carrying case according to a second embodiment of the present invention.

FIG. 3 is a view schematically illustrating a carrying case according to a second embodiment of the present invention. As illustrated, one or more guide rods 410, 420, 430, and 430 are respectively coupled to the inner surface of the first main body 100 and the inner surface of the second main body 200 so as to be parallel to a major axis. A pair of guide rods 410 and 420 or a pair of guide rods 430 and 440 may be separately installed. Rollers 411, 421, 431, and 441 are penetratively coupled to the guide rods 410, 420, 430, and 430, such that a mask M may be smoothly stored in the case 1000 while easily rolling in an S shape. Reference numeral 214 indicates a coupling member for the mask strap and the connection part. The rollers 411, 421, 431, and 441 may be made of copper to kill bacteria and viruses on the mask stored in the carrying case.

Figure 5:
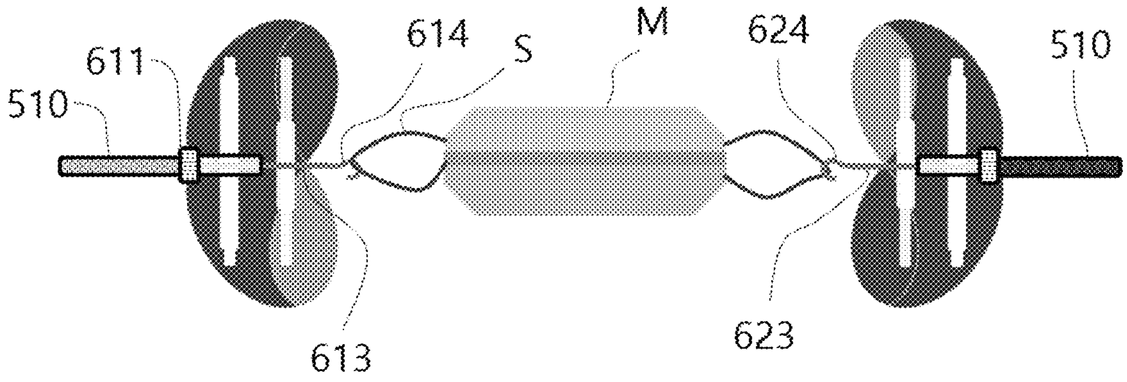
FIG. 5 is a view schematically illustrating a carrying case according to a third embodiment of the present invention.

FIG. 5 is a view schematically illustrating a carrying case according to a third embodiment of the present invention. The carrying case 1000 according to the third embodiment may have a connection part 600 provided inside the first and second main bodies 100 and 200 and configured to connect a mask strap S. The connection part 600 includes couplers 611 and 621 to couple the main bodies 100 and 200, and the couplers 611 and 621 are disposed in central regions of the inner surfaces of the main bodies 100 and 200 that face each other when the main bodies 100 and 200 are coupled. Connection strings 613 are connected to the couplers 611 and 621. Connection rings 614 are coupled to ends of the connection strings 613, so that the mask straps s may be hung on the connection rings 614. Two opposite ends of a connection strap 510 may be respectively connected to the couplers 611 and 621.

Figure 6:
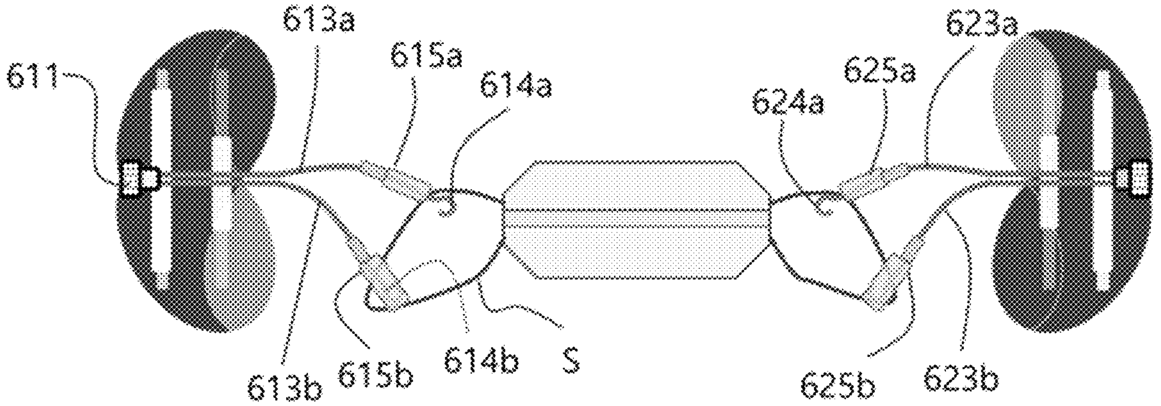
FIG. 6 is a view schematically illustrating a carrying case according to a fourth embodiment of the present invention.

FIG. 6 is a view schematically illustrating a carrying case according to a fourth embodiment of the present invention. As illustrated, in the carrying case 1000 according to the fourth embodiment, a pair of connection strings 613*a*, 613*b*, 623*a*, and 624*b* may be respectively connected to the couplers 611 and 621. Connection rings 614*a*, 614*b*, 624*a*, and 624*b* are respectively coupled to ends of the connection strings 613*a*, 613*b*, 623*a*, and 624*b*, and connection ring protection covers 615*a*, 615*b*, 625*a*, and 625*b* each having a folded pipe shape may be coupled to expose or cover the connection rings 614*a*, 614*b*, 624*a*, and 624*b*.

Figure 7:
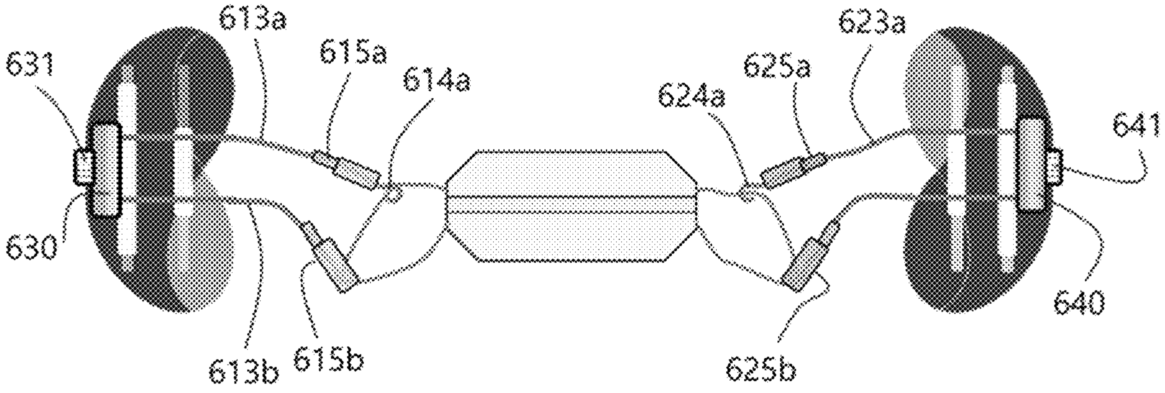
FIG. 7 is a view schematically illustrating a carrying case according to a fifth embodiment of the present invention.

FIG. 7 is a view schematically illustrating a carrying case according to a fifth embodiment of the present invention. As illustrated, in the carrying case 1000 according to the fifth embodiment, reel-shaped storage boxes 630 and 640 in which the connection strings 613 and 623 are semi-automatically wound are disposed, and automatic winding buttons 631 and 641 of the reel-shaped storage boxes 630 and 640 are disposed outside the main bodies 100 and 200, such that the connection strings 613 and 623 are automatically wound in the reel-shaped storage boxes 630 and 640 when the buttons 631 and 641 are operated.

Figure 4:
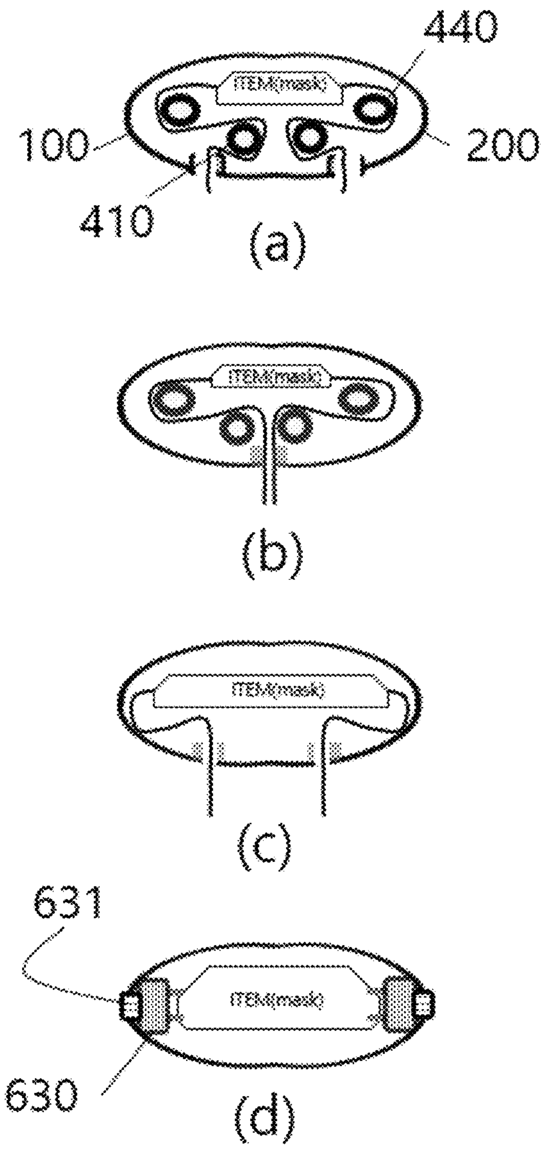
FIG. 4 is a cross-sectional view illustrating a usage state according to the embodiments of the present invention.

FIG. 4 is a cross-sectional view illustrating a usage state according to the present invention embodiments, in which FIG. 4A is a cross-sectional view illustrating an embodiment in which entrance holes for the connection strings 613 and 623 are respectively formed in the main bodies 100 and 200, FIG. 4B is a cross-sectional view illustrating an embodiment in which an entrance hole for the connection strings 613 and 623 are formed at one point between the main bodies 100 and 200, FIG. 4C is a cross-sectional view illustrating an embodiment in which no guide rod is provided, and FIG. 4D is a view illustrating a state in which a mask is stored in the carrying case 1000 according to the fifth embodiment illustrated in FIG. 7.

Figure 8:
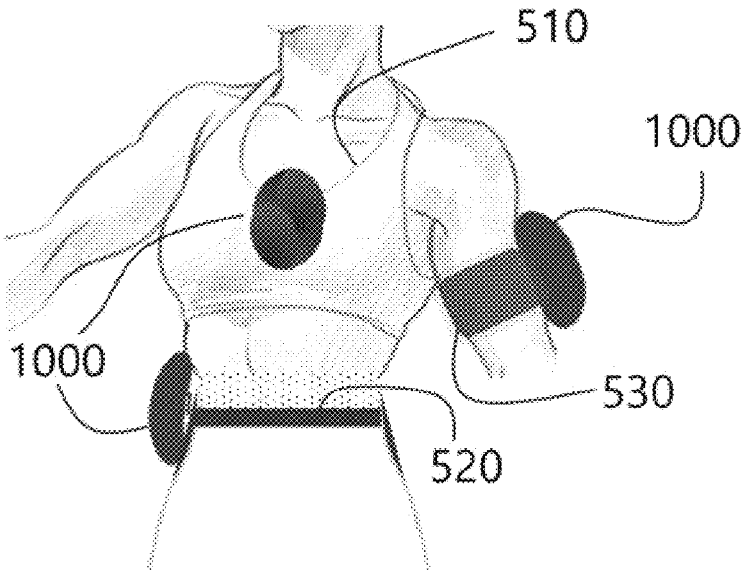
FIG. 8 is a view schematically illustrating a carrying case according to a sixth embodiment of the present invention.

FIG. 8 is a view illustrating a state in which the carrying case according to the embodiment of the present invention is worn. As illustrated, the necklace connection strap 510 may be coupled to the carrying case 1000, such that the user may wear the case 100 around his/her neck. In addition, a belt 520 may be coupled to the carrying case 1000, such that the user may wear the case 100 around his/her waist. In addition, an arm band 530 may be coupled to the carrying case 1000, such that the user may wear the case 100 around his/her arm.

Figure 9:
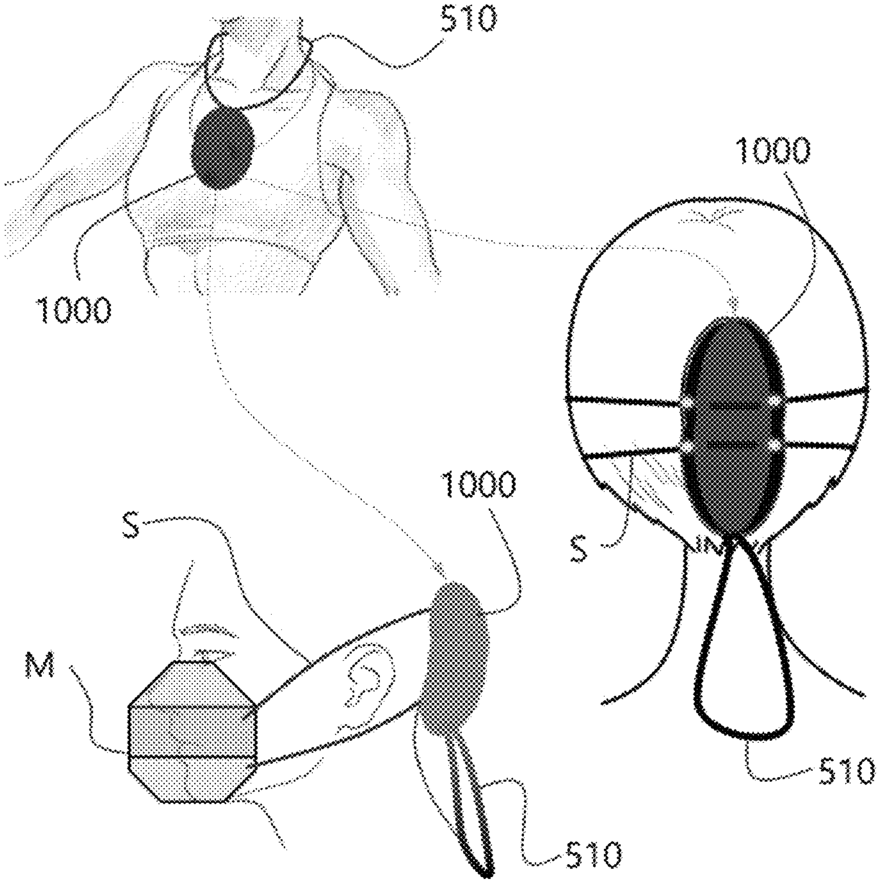
FIGS. 9 to 11 are views illustrating states in which the carrying cases according to the embodiments of the present invention are worn.

The carrying case 1000 illustrated in FIG. 9 is a mask-integrated type carrying case. As illustrated, an end of the strap s of the mask is fixed to the carrying case 1000. Therefore, the mask is stored in the carrying case 1000 worn around the neck by means of the necklace connection strap 510 when the user does not wear the mask. When the user wears the mask, the user may wear the mask by fixing the carrying case 1000, to which the end of the strap s is fixed, to a back side of his/her head without hanging the strap s on his/her ear.

Figure 10:
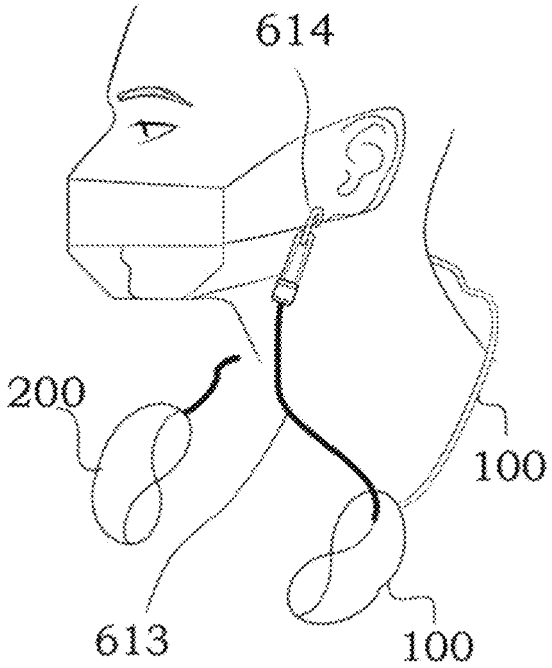
Figure 11:
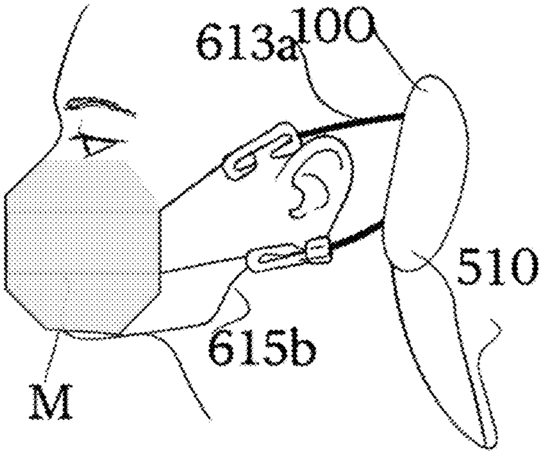

FIG. 10 is a view illustrating a state in which the carrying case according to the third embodiment of the present invention illustrated in FIG. 5 is worn, and FIG. 11 is a view illustrating a state in which the carrying case according to the fifth embodiment illustrated in FIG. 6 or 7 is worn. As illustrated, the connection straps 613 and 623 are coupled to the mask strap s. The main bodies 100 and 200 may be fixed to the back side of the head when the main bodies 100 and 200 are coupled. The main bodies 100 and 200 may be worn around the neck by means of the necklace connection strap 510 when the main bodies 100 and 200 are not coupled.

A sterilization device may be installed inside the carrying case 1000 and kill bacteria and viruses on the stored item by operating while the item is stored in the case 1000. The sterilization device may use a UV LED or a liquid or vapor phase sterilization method. In addition, a display may be installed on the outside of the carrying case 1000 to indicate information about storage time, mask usage time, and the like. In addition, wireless communication means, such as Wi-Fi or Bluetooth, may be provided to transmit or receive storage information. In addition, the carrying case 1000 may further include a location recognition device.

In the embodiment of the present invention, the carrying case is illustrated as an ellipsoid, but the shape of the carrying case is not limited thereto and may be formed in a hexahedral or polyhedral shape.

While the exemplary embodiments of the present invention have been described with reference to the accompanying drawings, those skilled in the art will understand that the present invention may be carried out in any other specific form without changing the technical spirit or an essential feature thereof. Therefore, it should be understood that the above-described embodiments are illustrative in all aspects and do not limit the present invention.

The invention claimed is:

1. A carrying case comprising:

a first main body having a semi-ellipsoidal shell shape; and a second main body having a semi-ellipsoidal shell shape corresponding to the first main body so that the second main body is coupled to the first main body to define an ellipsoid, wherein a coupling end of the first main body, which is coupled to the second main body, has two or more pairs of connected convex portions and two or more pairs of connected concave portions, such that a lateral side at a major axis side has a taegeuk shape, wherein a coupling end of the second main body has concave portions formed at positions corresponding to the convex portions of the first main body, and convex portions formed at positions corresponding to the concave portions of the first main body, and wherein one or two cut-out grooves having a preset length perpendicular to the coupling end are formed at one coupling end or two opposite coupling ends of the first main body and the second main body, wherein coupling members are respectively provided on the first main body and the second main body, and a connection part connected to a mask strap is coupled to the coupling members, wherein the connection part comprises: couplers coupled to central regions of the first main body and the second main body; connection strings respectively coupled to the couplers; and connection rings coupled to ends of the connection strings so as to be connected to the mask strap, and wherein a connection ring protection cover having a folded pipe shape is penetratively coupled to the connection string and covers the connection ring.

2. The carrying case of claim 1, wherein magnets having corresponding polarities are embedded in peripheries of the coupling ends of the first and second main bodies.

3. The carrying case of claim 1, wherein a radius of curvature of each of the concave and convex portions of the first and second main bodies is ½ or less of a minor axis of the ellipsoid.

4. A carrying case comprising:

a first main body having a semi-ellipsoidal shell shape; and a second main body having a semi-ellipsoidal shell shape corresponding to the first main body so that the second main body is coupled to the first main body to define an ellipsoid, wherein a coupling end of the first main body, which is coupled to the second main body, has two or more pairs of connected convex portions and two or more pairs of connected concave portions, such that a lateral side at a major axis side has a taegeuk shape, wherein a coupling end of the second main body has concave portions formed at positions corresponding to the convex portions of the first main body, and convex portions formed at positions corresponding to the concave portions of the first main body, and wherein one or two cut-out grooves having a preset length perpendicular to the coupling end are formed at one coupling end or two opposite coupling ends of the first main body and the second main body, wherein coupling members are respectively provided on the first main body and the second main body, and a connection part connected to a mask strap is coupled to the coupling members, wherein the connection part comprises: couplers coupled to central regions of the first main body and the second main body; connection strings respectively coupled to the couplers; and connection rings coupled to ends of the connection strings so as to be connected to the mask strap, and wherein reel-shaped storage boxes are respectively disposed inside the first main body and the second main body, and the connection strings are semi-automatically wound in the reel-shaped storage boxes.

5. A carrying case comprising:

a first main body having a semi-ellipsoidal shell shape; and a second main body having a semi-ellipsoidal shell shape corresponding to the first main body so that the second main body is coupled to the first main body to define an ellipsoid, wherein a coupling end of the first main body, which is coupled to the second main body, has two or more pairs of connected convex portions and two or more pairs of connected concave portions, such that a lateral side at a major axis side has a taegeuk shape, wherein a coupling end of the second main body has concave portions formed at positions corresponding to the convex portions of the first main body, and convex portions formed at positions corresponding to the concave portions of the first main body, and wherein one or two cut-out grooves having a preset length perpendicular to the coupling end are formed at one coupling end or two opposite coupling ends of the first main body and the second main body, and wherein one or more guide rods are respectively coupled to inner surfaces of the first and second main bodies so as to be parallel to a major axis of the ellipsoid, and rollers are penetratively coupled to the guide rods, respectively.

* * * * *